US009968277B2

(12) United States Patent
Weiss et al.

(10) Patent No.: US 9,968,277 B2
(45) Date of Patent: May 15, 2018

(54) MAGNETIC RESONANCE GUIDANCE OF A SHAFT TO A TARGET ZONE

(75) Inventors: Steffen Weiss, Hamburg (DE); Ronaldus Frederik Johannes Holthuizen, Best (NL); Sascha Krueger, Hamburg (DE); Peter Koken, Hamburg (DE); Daniel Wirtz, Hamburg (DE); Thomas Erik Amthor, Hamburg (DE); Falk Uhlemann, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 311 days.

(21) Appl. No.: 14/007,990

(22) PCT Filed: Apr. 4, 2012

(86) PCT No.: PCT/IB2012/051661
§ 371 (c)(1),
(2), (4) Date: Sep. 27, 2013

(87) PCT Pub. No.: WO2012/137148
PCT Pub. Date: Oct. 11, 2012

(65) Prior Publication Data
US 2014/0018664 A1 Jan. 16, 2014

(30) Foreign Application Priority Data
Apr. 7, 2011 (EP) .................................... 11161457

(51) Int. Cl.
*A61B 5/055* (2006.01)
*G01R 33/28* (2006.01)
(Continued)

(52) U.S. Cl.
CPC .............. *A61B 5/055* (2013.01); *A61B 5/064* (2013.01); *A61B 5/6832* (2013.01); *A61B 5/72* (2013.01);
(Continued)

(58) Field of Classification Search
CPC .................................................. A61B 5/6832
See application file for complete search history.

(56) References Cited

U.S. PATENT DOCUMENTS 6,119,032 A * 9/2000 Martin ............... A61B 17/3403
600/411
6,302,990 B1 * 10/2001 Nelson ..................... 156/244.13
(Continued)

FOREIGN PATENT DOCUMENTS

JP           453533 A    2/1992
JP     2002058658 A     2/2002
(Continued)

OTHER PUBLICATIONS

Kuehne, Titus et al "Pair of Resonant Fiducial markers for Localization of Endovascular Catheters at all Catheter Orientations", Journal of Magnetic Resonance Imaging, vol. 17, No. 5, May 2003, pp. 620-624.
(Continued)

*Primary Examiner* — Farshad Negarestan

(57) ABSTRACT

A medical apparatus (1100) comprising a magnetic resonance imaging system and an interventional device (300) comprising a shaft (302, 1014, 1120). The medical apparatus further comprises a toroidal magnetic resonance fiducial marker (306, 600, 800, 900, 1000, 1122) attached to the shaft. The shaft passes through a center point (610, 810, 908, 1006) of the fiducial marker. The medical apparatus further comprises machine executable instructions (1150, 1152, 1154, 1156, 1158) for execution by a processor. The instructions cause the processor to acquire (100, 200) magnetic resonance data, to reconstruct (102, 202) a magnetic resonance image (1142), and to receive (104, 204) the selection of a target volume (1118, 1144, 1168). The instructions further cause the processor to repeatedly: acquire (106, 206) magnetic resonance location data (1146) from the fiducial
(Continued)

marker and render (108, 212) a view (1148, 1162) indicating the position of the shaft relative to the target zone.

10 Claims, 9 Drawing Sheets

(51) Int. Cl.
*A61B 5/06* (2006.01)
*A61B 5/00* (2006.01)
*G01R 33/34* (2006.01)

(52) U.S. Cl.
CPC ...... *G01R 33/287* (2013.01); *G01R 33/34084* (2013.01)

(56) References Cited

U.S. PATENT DOCUMENTS

| | | | |
|---|---|---|---|
| 6,419,680 B1 * | 7/2002 | Cosman | A61B 19/54 378/162 |
| 6,574,497 B1 | 6/2003 | Pacetti | |
| 7,276,905 B2 | 10/2007 | Tamaroff et al. | |
| 2001/0011889 A1 | 8/2001 | Golan | |
| 2003/0220557 A1 * | 11/2003 | Cleary et al. | 600/409 |
| 2008/0242978 A1 * | 10/2008 | Simon | A61B 19/52 600/426 |
| 2010/0063383 A1 | 3/2010 | Anderson et al. | |

FOREIGN PATENT DOCUMENTS

| | | |
|---|---|---|
| JP | 2002272700 A | 9/2002 |
| JP | 2004248683 A | 9/2004 |
| WO | 2012160486 A2 | 11/2012 |

OTHER PUBLICATIONS

Rea, Marc et al "Sub-Pixel Localisation of Passive Micro-Coil Fiducial Markers in Interventional MRI", Magnetic Resonance Material in Physics, Biology and Medicine. vol. 22, No. 2, Sep. 2008, pp. 71-76.

Hegde, Sanjeet et al "Interactive MR Imaging and Tracking of Catheters with Multiple Tuned Fiducial Markers", Journal of Vascular and Interventional Radionlogy, vol. 17, No. 7. Jul. 2006, pp. 1175-1179.

Wonneberger, U. et al "Clinically Usable Tool for Dynamic Scan-Plane Tracking for Real-Time MRI-Guided Needle Interventions in a High-Field-Open MRI System", ISMRM, 3395, 2010.

Schaeffter, T. et al "Automatic Scan Plane Definition for Frameless MR-Stereotaxy on a Clinical Scanner using an Active Surgical Device Holder", ISMRM 1999.

Fischbach, F. et al "MR-Guided Ablative Therapy of Malignant Liver Tumors Employing the Panorama HFO open MR Scanner", Clinical Applications, Medicamundi vol. 54, No. 3, 2010, pp. 35-40.

Fischbach, F. et al "MR-Guided Freehand Biopsy of Liver Lesions with Fast Continuous Imaging using a 1.0-T Open MRI Scanner: Experience in 50 Patients", Cardiovacsular Interventional Radiology, 2010.

Coutts, Glyn A. et al "Integrated and Interactive Position Tracking and Imaging of Interventional Tools and Internal Devices using Small Fiducial Receiver Coils", Magnetic Resonance in Medicine, vol. 40, 1998, pp. 908-913.

Ackerman, J.L. et al "Rapid 3D Tracking of Small RF Coils", ISMRM 1986.

* cited by examiner

MAGNETIC RESONANCE GUIDANCE OF A SHAFT TO A TARGET ZONE

CROSS-REFERENCE TO PRIOR APPLICATIONS

This application is the U.S. National Phase application under 35 U.S.C. § 371 of International Application No. PCT/IB2012/051661, filed on Apr. 4, 2012, which claims the benefit of European Patent Application No. 11161457.4, filed on Apr. 7, 2011. These applications are hereby incorporated by reference herein.

TECHNICAL FIELD

The invention relates to magnetic resonance imaging, in particular to the use of magnetic resonance to guide a shaft to a target zone within a subject.

BACKGROUND OF THE INVENTION

The availability of interactive real-time MRI and MR-conditional instruments has lead to an increasing use of MR-guidance especially in transcutaneous procedures performed with needles or linear ablation probes. Besides the lack of ionizing radiation MR-guidance offers a number of advantages for such procedures, the most important one being the soft tissue contrast and full tomographic capability of MR, if compared with CT or US. State-of-the-art clinical MR-guided percutaneous interventions use pre-operative 3D MR images to plan the device path, then stereotactic device guides to align the device with the target and to guide its insertion, which is mostly performed outside the MR bore. Finally, MR is used to confirm that the device has reached the target.

Because stereotactic procedures are prone to registration errors due to patient motion and needle bending, and because they involve a complicated workflow (patient movement into and out of bore), advanced centers are now practicing so-called free-hand procedures, in which the device is advanced without any physical stereotactic device guide under real-time image guidance inside the MR. This is facilitated by dedicated MR sequences that visualize the target lesion and the device with high conspicuity and by the availability of open MR systems.

In Coutts et. at. "Integrated and Interactive Position Tracking and Imaging of Interventional Tools and Internal Devices Using Small Fiducial Receiver Coils," Magnetic Resonance in Medicine, vol. 40, 1998, pages 908-913, a method of tracking the position of a rigid device within a magnetic resonance scanner is disclosed. The position tracking is performed by means of two or three small magnetic resonance receiver coils attached to individual receiver channels.

SUMMARY OF THE INVENTION

The invention provides for a medical apparatus, a computer program product, and a magnetic resonance fiducial marker in the independent claims. Embodiments are given in the dependent claims.

Some embodiments of the invention may be particularly advantageous, because alignment of the imaging slices with needle and/or target lesion may be performed automatically. Manual adjustment of slices is current practice, but requires that the interventionist communicates the requested slice adjustments to the MR operator outside the MR room, which is not trivial and requires an experienced and well attuned team. Means to support, automate, and improve the workflow of such free-hand interventions are mandatory to foster a wide-spread use.

The toroidal shape of the fiducial markers of embodiments of the invention allows measurement of the position and/or orientation of the needle axis with only one or two markers but without blocking the needle axis as would be the case for point-like markers. Hence, embodiments of the invention may be compatible with any needle-type device and, additionally, secondary devices can be introduced, e.g. a stylet or biopsy device into a hollow needle.

Using individual light markers as the device guide reduces its size and vastly increases the mechanical flexibility of wiring, which is essential to allow for uncompromised maneuverability and minute haptic feedback as required when advancing the device into the patient. The device guide does not require additional attention (holding/steering/aligning etc.) by the physician and the needle-type devices can be manipulated as usual.

Embodiments of the invention may provide for an interventional device with reduced weight and/or an interventional device which is more easily controlled with a single hand. Current interventional devices may have a relatively large size. The size is caused by the necessity to incorporate at least three markers with sufficient mutual distance to measure the position and orientation of the device with sufficient accuracy. This is important to achieve proper alignment of the imaging slice with the device. Even small angular errors can otherwise lead to a displacement between needle and slice inside the patient. Target lesions can be located as deeply as 20 cm inside the patient. Embodiments of the invention may provide a means of overcoming this limitation. A large size of the device is disadvantageous especially when several needles and catheters are applied in one patient close to each other as for HDR brachytherapy.

Embodiments of the invention may reduce the number of wires to the inverventional device with respect to current interventional devices. Current devices which rely on the use of multiple fiducialmarkers may have clumsy wiring. The use of several markers in the device results in a heavy and in-flexible connection cable with about 1.5 cm diameter and respectively large and heavy cable traps to avoid dangerous shield currents. Embodiments of the invention may provide a means of overcoming this limitation.

Embodiments of the invention may provide for an interventional device where the fiducial marker is attached to the shaft or needle of the interventional device. With some current devices, the size and weight of the device and its wiring and the relative in-flexibility of the wiring have lead to concerns to rigidly attach the needle to the guide itself as initially intended. Instead, a bar with a V-shaped groove is used to which the interventionist aligns the needle with his second hand. However, tests have shown that handling of needle and guidance tool with two hands is uncomfortable and for some users even totally unfeasible. Embodiments of the invention may provide a means of overcoming this limitation.

Embodiments of the invention may provide for improved maneuverability and haptics of the interventional device. Free-hand needle interventions depend on a minute haptic feedback which is required when advancing the needle into the patient. The interventionist must be able to "feel" the crossing of internal interfaces. The size of the device, the weight and in-flexibility of the relatively thick cable, and the need to use two hands to maneuver needle and tool vastly hampers maneuverability and haptics. Embodiments of the invention may provide a means of overcoming this limitation.

Embodiments of the invention may reduce the likelihood that a fiducial marker is out of the field of view, or imaging region, of a magnetic resonance imaging system. In some current implementations, guidance tools of relatively large size are attached/positioned proximally to and about aligned with the needle, such that the overall length of the assembly from needle tip to the most proximal marker is in the order of 30 cm. The lesion may be as deep as 15 cm inside the patient. During entry of the needle into the skin, all active tracking markers as well as the lesion should be in the imaging volume of the MR scanner, which is typically a sphere of less than 45 cm diameter. The patient must be very carefully positioned to achieve this, and even if so, the interesting objects are lying at the edge of the imaging sphere with associated low SNR and geometric distortions. Embodiments of the invention may provide a means of overcoming this limitation.

Embodiments of the invention may provide for an improved orientation independence of the fiducial marker. Current active markers receive signal from a water-filled bead contained in a solenoid coil. If the solenoid is aligned with B0, the SNR of the signal drops vastly, because the transverse components of the B1-sensitivity of the solenoid are very small. Embodiments of the invention may provide a means of overcoming this limitation.

Embodiments of the invention may provide for an intuitive viewing plane control. Surprisingly, some interventionists have difficulties to cope with the fact, that they have full 6D control of the scan planes, since the planes stay "rigidly attached" to the tool. This type of control requires that the operator keeps the tool in a defined position and orientation. This is very different from the previous situation, where only the needle was held and maneuvered, and the operator at the console was in control of the scan planes. Embodiments of the invention may provide a means of overcoming this limitation.

The invention may provide for a light-weight and small device guide is that is equipped with a single toroid-shaped active marker. It may be used in combination with a similarly shaped marker positioned near or adhering to the skin at the device entry point. The marker with toroidal shape is crossed centrally by the needle-type device to be guided such that the center of gravity of its signal distribution lies on the needle axis. This allows localizing the respective point on the needle axis with a single marker channel and irrespective of the orientation of the guide with respect to B0. Using only a single such marker at the device guide reduces its size and vastly increases the flexibility of wiring.

The scan planes for image guidance are defined to contain the two points defined by the two markers, i.e., the position of the needle hub and of the skin entry point. Two nearly perpendicular planes are used for guidance as before, e.g. one para-coronal slice and one para-transverse slice in a liver intervention. The para-coronal slice is defined as to contain both marker positions and the FH axis. The para-transverse is defined to contain the AP axis if the needle is mainly advanced in RL direction and vice versa.

The set-up may consist of a light-weight and small guide marker and a skin marker. Both markers have a central opening to let the needle pass. Both markers may be equipped with a plug that can be plugged into a socket at the surface coil. This minimizes cable length and workflow.

Note, that the toroidal shape of the signal volume allows measuring the needle axis with only two markers but without blocking the needle axis as would be the case for two point-like markers. Hence, all needle-type devices can be guided accurately and, in addition, secondary devices can be introduced any time during the procedure with the guide still in use, e.g. a stylet or biopsy device into a hollow needle or guidewires as necessary for Seldinger introduction techniques.

A possible workflow for using embodiments of the invention may be:

1. Interventionist defines and marks skin entry point, either with the conventional "finger-pointing method" or by moving the skin marker across the skin. Finally, the entry point is marked by a pen, prepared for insertion (disinfection, local anesthesia, actually may have been performed earlier) and the skin marker is attached to the prepared entry site. Note, that using the skin markers together with the known coordinates of the e.g. target tumor already allows appropriate real-time imaging along the estimated needle path in e.g. one para-transversal and one para-coronal image slice and thus provides optimal guidance during this interactive planning step.

2. Needle tip is put onto the entry point.

3. Needle shaft is aligned with the planned trajectory by moving the needle hub. This can be achieved in two ways: a) The MR system tracks the position of the markers and either displays the resulting trajectory as a line on pre-operative images (navigational display). b) Para-coronal and/or para-transversal real-time slices are acquired defined as described above. When arrived at the correct trajectory, the needle should aim to the target lesion, which can be confirmed by either the navigational display or the real-time slice(s).

4. Needle is advanced into the body with continuous image control. This allows to see and adjust for needle deviations, needle bending, physiological motion.

In an alternate workflow the entry point of the needle is defined virtually using a software package and active needle guidance is used to position the needle at the correct entry point and trajectory. For this workflow both markers are placed on the needle, and the entry point may not have to be marked physically.

In one embodiment, the receive coils can be shaped as simple circular coils around the toroidal signal volume. This simpler coil set-up is allowable, if it is excluded by the type of intervention, that the circular axis is aligned with B0, which would result in a low signal. In the liver interventions performed in a 1Tesla magnetic resonance imaging system this is the case, and the simpler coil set-up can be used.

In one embodiment, the skin marker is equipped with such a circular receive coil and lacks an own toroidal signal volume. Instead, the skin is used as signal source.

In one embodiment, the marker preferably equipped with such a simple circular coil is a disposable device.

In one embodiment, the coil of the skin marker is not wired to an MR receiver, but made resonant with a capacitor and its signal is detected via inductive coupling to the surface coil. Active decoupling and a difference measurement may be used to reduce global background signal.

The alignment of the marker centers with the needle axis can be based on a sterile approach using single-use small adhesive patches a little bit larger in size than the markers.

The patches will be attached to the markers parallel to the marker plane from both sides so:

a.) They fully encapsulate the marker and thus render the assembly sterile
b.) The adhesive faces touch each other at the bore region of the markers
c.) Needle-type devices can be poked through the markers center where the adhesive patches touch each other and the markers thus stay aligned with the needle axis but can be slid along the needle to avoid the FOV problem or to move them to a more favorable position (examples: move marker or marker wiring to different position in case of space limitations occurring during the intervention).
d.) Patches can be removed and markers and needle-type device can be separated while the needle-type device is still inserted.

In one embodiment the circular skin marker features a gap such as to remove the marker easily sideways after complete insertion of the guided device and reuse the active skin marker for consecutive workflow steps.

In one embodiment a multitude of markers with distinct coding (e.g. via shape, signal . . . ) is available during the procedure. This allows to identify different inserted devices via their transcutaneous port position. In conjunction with the stored device orientation during insertion, (real-time) imaging planes can be easily recalled/adjusted to the respective device.

In one embodiment, both markers are on the needle instead of 1 on the needle and one on the skin to provide a 1-hand 1-movement workflow where it is no longer required to manually place the skin marker as a separate workflow step.

In one embodiment, a plastic spacer prevents that two markers come too close together to ensure accuracy of the imaged trajectory is maintained.

In one embodiment, the needle insertion depth is calculated from the marker that moves with the needle hub and marker that is held in position by the skin and the known location of the markers with respect to the needle.

Assuming a measurement precision of about 1 mm for the needle coordinates at the position of the two markers, the expected alignment error of the imaging planes will typically be small compared to the width of the image artifact caused by the needle. Only in a situation when the two markers have to be moved very close together, the tip of a long needle may be missed in the images. The following two embodiments are proposed to correct this possible misalignment:

1. The described active tracking method using the two markers is combined with a passive tracking method employing detection of the needle pointing direction via image analysis
2. A software tool is used to store a history of needle coordinates during needle progression and to guess the best image plane orientation. Alternatively or additionally, the target (e.g. tumor) coordinates which had been determined before the start of the intervention (as mentioned under "workflow" above) can be used as a third marker point when the needle tip approaches the target.

Embodiments of the invention may have the following advantages: The guide marker (magnetic resonance fiducial marker) is small, light-weight, and equipped with minimal wiring. The marker is centrally attached to the needle. As a consequence, the interventionist has nearly as fine haptic feedback and freedom to maneuver as with a bare needle. The "Out-of-FOV-problem" is reduced/solved because the length of the device reduces to the length of the needle. For very long needles, the guide marker may even be allowed to slide on the needle shaft, bringing it nearer to the isocenter. The marker orientation problem is solved because there are always two zones within the toroid where the Biot-Savart-field of the toroidal coil is transverse. In these zones, there is maximum signal. There is no marker orientation in which the signal vanishes. The problem of unintuitive scan plane control is solved, since the operator is back to the used way of mainly maneuvering the needle itself with only one hand. The second hand is free to assist in this or for other purposes. The large distance between the guide marker and the skin marker during the targeting phase and the phase of initial needle insertion results in a high targeting accuracy. The large signal volume of the toroidal markers compared to beed-like markers potentially results in a higher accuracy of position measurement. The markers may be implemented as single-use devices, enabling to generate device-based revenues. The invention can be applied to all MR-guided transcutaneous interventions performed with linear-shaped devices.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. References to a computer-readable storage medium should be interpreted as possibly being multiple computer-readable storage mediums. Various executable components of a program or programs may be stored in different locations. The computer-readable storage medium may for instance be multiple computer-readable storage medium within the same computer system. The computer-readable storage medium may also be computer-readable storage medium distributed amongst multiple computer systems or computing devices.

'Computer memory' or 'memory' is an example of a computer-readable storage medium. Computer memory is any memory which is directly accessible to a processor. Examples of computer memory include, but are not limited to: RAM memory, registers, and register files. References to 'computer memory' or 'memory' should be interpreted as possibly being multiple memories. The memory may for instance be multiple memories within the same computer system. The memory may also be multiple memories distributed amongst multiple computer systems or computing devices.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa. References to 'computer storage' or 'storage' should be interpreted as possibly being multiple storage. The storage may for instance be multiple storage devices within the same computer system or computing device. The storage may also be multiple storages distributed amongst multiple computer systems or computing devices.

A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses a interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

The invention provides for a medical apparatus comprising a magnetic resonance imaging system for acquiring magnetic resonance data from a subject. The medical apparatus further comprises an interventional device comprising a shaft. The shaft is adapted for being inserted into the subject. For instance the shaft may be a needle or other long narrow structure which is able to be inserted into the subject. In some embodiments the shaft may be able to pierce the skin or surface of a subject. The medical apparatus further comprises a first magnetic resonance fiducial marker attached to the shaft. In some embodiments the first magnetic resonance fiducial marker is removable. For instance the first magnetic resonance fiducial marker may be able to slide along the shaft and be removed from an end of the shaft. The first magnetic resonance fiducial marker is toroidal. A toroid is a shape which is formed by rotating a two-dimensional shape about an axis. For instance if a circle is rotated about the axis the toroid is a torus. Squares, rectangles, ovals or other shapes may also be rotated about the axis. By saying that the first magnetic resonance fiducial marker is toroidal it is also common to say that the first magnetic resonance fiducial marker is substantially toroidal or a component of the first magnetic resonance fiducial marker is toroidal. In some embodiments a container which is toroidally-shaped is used to form the first magnetic resonance fiducial marker. In other embodiments a circular or washer-shaped section of circuit board or Teflon is used to form the first magnetic resonance fiducial marker.

The shaft passes through a centre point of the first magnetic resonance fiducial marker. The centre point may have a hole or other structure which is used for guiding the shaft through the centre point. In other embodiments the first magnetic resonance fiducial marker may comprise paper or a thin layer of plastic which can be pierced by the shaft and the centre point is marked on the paper or the thin plastic.

The medical apparatus further comprises a processor for controlling the medical apparatus. The medical apparatus further comprises a memory storing machine executable instructions for execution by the processor. Execution of the instructions causes the processor to acquire the magnetic resonance data. This may be achieved by the processor controlling the magnetic resonance imaging system and sending appropriate instructions which cause it to acquire the magnetic resonance data. Execution of the instructions further causes the processor to reconstruct the magnetic resonance data into a magnetic resonance image. This may be achieved using a software module for reconstructing the magnetic resonance data into a magnetic resonance image.

Execution of the instructions further causes the processor to receive the selection of a target volume within the magnetic resonance image. The selection of the target volume can be performed manually. For instance a target volume may be identified using a graphical user interface which selects a region or a portion of the magnetic resonance image as the target volume. In yet other embodiments the selection of the target volume may be performed automatically by an image segmentation module. Various models and methods known in the art may be used to identify the location of anatomical structures.

In another embodiment execution of the instructions further cause the processor to repeatedly acquire magnetic resonance location data from the first magnetic resonance fiducial marker using the magnetic resonance imaging system. This may be achieved in several different ways depending upon how the first magnetic resonance fiducial marker is constructed. For instance various gradient fields may be used to spatially encode magnetically polarizable material within a vessel of the first magnetic resonance fiducial marker. In this case a coil wrapped around the toroidal structure may be used to acquire the magnetic resonance location data. In yet other embodiments the toroidal structure of the first magnetic resonance fiducial marker may be located in a normal magnetic resonance image. The magnetic resonance location data is descriptive of the location of the first magnetic resonance fiducial marker. Execution of the instructions further causes the processor to repeatedly render a view indicating the position of the shaft relative to the target zone on a display device. The view is determined using at least the location data and the location of the target volume. This embodiment is particularly advantageous because the toroidal shape of the first magnetic resonance fiducial marker allows its position and/or orientation to be determined. This greatly reduces the number of magnetic resonance fiducial markers necessary to identify the location of the shaft of the interventional device. This for instance allows a reduction in the weight of the interventional device and also its size which makes it easier to fit within an imaging zone of the magnetic resonance imaging system. It may also be more convenient and ergonomic for a physician or other medical professional to use the interventional device.

In another embodiment execution of the instructions further cause the processor to repeatedly re-acquire the magnetic resonance data. Execution of the instructions further causes the processor to repeatedly reconstruct the magnetic resonance image using the re-acquired magnetic resonance data. The view comprises the magnetic resonance image. In this embodiment the magnetic resonance data is repeatedly re-acquired and used to display an updated or fresh magnetic resonance image. This may be advantageous because the subject may have internal or external motion which is in motion during the use of the interventional device. This may provide for a more accurate use of the interventional device.

In another embodiment execution of the instructions further causes the processor to repeatedly re-determine the location of the target zone using the magnetic resonance data. For instance an image segmentation module may be used to identify the location of the target zone automatically in some embodiments. This may be advantageous because the subject may have internal and/or external motion which causes the location of the target zone to change as a function of time.

In another embodiment the first magnetic resonance fiducial marker comprises a magnetic resonance receive coil surrounding a toroidal magnetic resonance signal volume. This embodiment is advantageous because the magnetic resonance receive coil can pick up the magnetic resonance signal from the toroidal magnetic resonance signal volume and be used to accurately locate the position and/or orientation of the first magnetic resonance fiducial marker.

In another embodiment the first magnetic resonance fiducial marker comprises a resonant coil and capacitor. In some embodiments, the resonant coil may be toroidally shaped or circularly shaped. By toroidally-shaped the resonant coil and capacitor may be formed on a substrate, circuit board, or piece of Teflon which is toroidal or substantially toroidal in shape. It may also be used to indicate that the coil is toroidal or substantially toroidal in shape. This embodiment may be advantageous because it can be used to form a compact magnetic resonance fiducial marker which has its position and/or orientation identified.

In another embodiment the apparatus further comprises a second magnetic resonance fiducial marker. The second magnetic resonance fiducial marker is adapted for guiding the shaft through a second centre point of the second magnetic resonance fiducial marker. The first centre point is through the first magnetic resonance fiducial marker and the second centre point is the centre point of the second magnetic resonance fiducial marker. The location data is further descriptive of the location of the second magnetic resonance fiducial marker. This embodiment is particularly advantageous because it is easier to identify the location of the centre point of a magnetic resonance fiducial marker than to identify both its centre point and its orientation. By simply identifying the location of the first and second centre points the orientation of the shaft of the interventional device is determined.

In another embodiment the second magnetic resonance fiducial marker comprises a toroidal magnetic resonance receive coil. In this embodiment it is not necessary for the receive coil to surround a magnetic resonance signal volume. This may be the case if the second magnetic resonance fiducial marker is placed on the skin or a surface of the subject. The subject may then function as the signal volume for the second magnetic resonance fiducial marker.

In another embodiment the second magnetic resonance fiducial marker comprises a toroidal magnetic resonance receive coil surrounding a second toroidal magnetic resonance signal volume. This embodiment may be advantageous because the magnetic resonance receive coil is able to receive magnetic resonance signals from the second signal volume which allows the determination of the location of its centre point and/or its orientation.

In another embodiment the second magnetic resonance fiducial marker comprises a toroidally-shaped resonant coil and capacitor. This embodiment has the same advantages as for the first magnetic resonance fiducial marker that was formed using a toroidally-shaped resonant coil and capacitor.

In another embodiment the second magnetic resonance fiducial marker is adapted to be attached to the surface of the subject. This may be particularly beneficial because the second magnetic resonance fiducial marker may be used to identify an entry point of the shaft into the subject.

In another embodiment the second magnetic resonance fiducial marker is adapted to be attached to an entry point of the shaft.

In another embodiment the apparatus further comprises a spacer to separate the first magnetic resonance fiducial marker and the second magnetic resonance fiducial marker.

This embodiment may be advantageous because it may allow for more accurate identification of the orientation of the shaft. For instance as the first and second centre points become closer to each other the margin of error used to calculate the orientation of the shaft becomes larger. By placing a spacer between the first magnetic resonance fiducial marker and the second magnetic resonance fiducial marker the error in the calculated location of the shaft can be kept below a predetermined threshold.

In another embodiment execution of the instructions further cause the processor to locate the first centre point and the second centre point using the magnetic resonance location data. Execution of the instructions further causes the processor to calculate a shaft position and orientation using at least the located first centre point and the located second centre point. The location data comprises the shaft position and/or orientation. This embodiment is particularly advantageous because the location of two points of the shaft allow its position and its orientation in space to be determined.

In another embodiment execution of the instructions further cause the processor to determine an orientation of the first magnetic resonance fiducial marker using the magnetic resonance location data. For instance the location of the first centre point may be determined. Execution of the instructions further cause the processor to calculate a shaft position using at least the located first centre point and the orientation of the first magnetic resonance fiducial marker. The toroidal shape allows the orientation of the first magnetic resonance fiducial marker to be determined in space. As was mentioned previously this may be very advantageous because it allows the identification of the location and/or orientation of the shaft with a single magnetic resonance fiducial marker.

In another embodiment the view is two-dimensional. By this it is meant that the view is a representation of a two-dimensional slice of the magnetic resonance data. Execution of the instructions further causes the processor to receive a selection of a shaft entry point in the magnetic resonance data. The shaft entry point may be identified in several different ways. For instance if it is present the shaft entry point may be identified using the second magnetic resonance fiducial marker if it is attached to a surface or skin of the subject. The shaft entry point may also be identified in a magnetic resonance image by a physician or operator using a human interface device such as a mouse. Receiving the selection of the shaft entry point may also be achieved by using image segmentation or recognition to identify the location of where the shaft enters the subject. The shaft entry point is descriptive of the location where the shaft enters the subject. The view is determined at least using the shaft entry point. This embodiment is advantageous because once the shaft has been inserted into the subject the shaft entry point does not change. The subject may move but the shaft entry point relative to the anatomy of the subject remains constant until the shaft is removed from the subject.

In another embodiment execution of the instructions further cause the processor to receive viewing plane offset and angulation commands. Typically the magnetic resonance data is acquired for a three-dimensional volume. During the procedure using the interventional device physicians or other healthcare professionals typically prefer to have a two-dimensional slice of the data which they see. By issuing plane offset and/or angulation commands the physician or healthcare professional can adjust and select which plane they would like to see during the performing of the procedure. Execution of the instructions further cause the processor to adjust the view using the viewing plane offset and angulation commands. This embodiment may be particularly advantageous because the view may be selected in some embodiments automatically by identifying the location of the shaft entry point and/or the target zone. The viewing plane offset and angulation commands can be given relative to the location of the target volume and/or the shaft entry point. This allows for the adjusting and optimal display of data during the procedure.

In another embodiment execution of the instructions further cause the processor to display a projection of the shaft onto the view. This may be extremely advantageous because the shaft may be out of the plane of the view. By projecting the shaft onto the view the physician or other healthcare professional is given additional information useful for guiding the shaft to the target zone.

In another embodiment color coding of the shaft is used to visualize which parts of the shaft are in front of, inside of, and/or behind the image plane. This is particularly useful as it provides additional information and allows a physician to better guide the shaft to the target zone. For instance a false color map could be used to indicate how far out of the plane a particular portion of the shaft is.

In another embodiment the magnetic resonance image is rendered as a three-dimensional image. This may be a three-dimensional image rendered on a two-dimensional display or the three-dimensional image may be rendered in three dimensions using a three-dimensional display or glasses which show the three-dimensional image to the physician or other healthcare professional.

In another embodiment the medical device further comprises a surface coil for receiving the magnetic resonance data. This may be particularly advantageous because the surface coil may be placed surrounding the location where the shaft enters the subject's body. The surface coil then surrounds a second magnetic resonance fiducial marker as it is placed on the surface of the subject. For certain embodiments, particularly when the second magnetic resonance fiducial marker comprises a toroidally-shaped resonance coil and capacitor, the surface coil may be used to easily identify the location of the magnetic resonance fiducial marker.

In another embodiment the interventional device is a needle.

In another embodiment the interventional device is a linear ablation probe.

In another embodiment the interventional device is a cryoprobe. A cryoprobe supplies cryogenic fluid or cools a vicinity of the probe tip to cryogenic temperatures to cool tissues to the point of ablation.

In another embodiment the interventional device is a laser ablation probe.

In another embodiment the interventional device is a biopsy needle.

In another embodiment the interventional device is a hollow needle.

In another embodiment the interventional device is a microwave probe. The microwave probe is adapted for delivering microwave energy to tissue in the vicinity of the tip of the shaft.

In another embodiment the interventional device is a guide wire delivery system. The guide wire may for instance be delivered using a hollow needle or other structure. The guide wire may then be used to deliver another interventional apparatus to the target zone.

In another aspect the invention provides for a computer program product comprising machine executable instructions for execution by a processor of a medical apparatus.

For instance the computer program product may be stored on a computer-readable storage medium. The medical apparatus comprises a magnetic resonance imaging system for acquiring magnetic resonance data from a subject. The medical apparatus further comprises an interventional device comprising a shaft. The shaft is adapted for being inserted into the subject. The medical apparatus further comprises a first magnetic resonance fiducial marker attached to the shaft. The first magnetic resonance location marker is toroidal. The shaft passes through a first centre point of the first magnetic resonance fiducial marker. Execution of the instructions causes the processor to acquire the magnetic resonance data. Execution of the instructions further causes the processor to reconstruct the magnetic resonance data into a magnetic resonance image. Execution of the instructions further causes the processor to receive the selection of a target volume within the subject. Execution of the instructions further cause the processor to repeatedly acquire magnetic resonance location data from the first magnetic resonance location marker using the magnetic resonance imaging system. The magnetic resonance location data is descriptive of the location of the first magnetic resonance fiducial marker. Execution of the instructions further causes the processor to repeatedly render a view indicating the position of the shaft relative to the target zone on a display device. The view is determined using at least the location data and the location of the target volume.

In another aspect the invention also provides for a method and a computer-implemented method for performing the aforementioned computer program product.

In another aspect the invention provides for a magnetic resonance fiducial marker adapted to attach to a shaft. The first magnetic resonance location marker is toroidal. The shaft is adapted to pass through a centre point of the magnetic resonance fiducial marker. This embodiment is advantageous because the toroidal magnetic resonance location marker may be used to identify both the location and orientation of the shaft using a single magnetic resonance location marker. The orientation or location of the shaft is also very easily identified using two magnetic resonance location markers. For instance the shaft may simply be able to be slid into a slot or hole at the centre point.

In another embodiment the magnetic resonance fiducial marker comprises a central support for guiding the shaft. The central support is adapted to be detached from the magnetic resonance fiducial marker. This is particularly advantageous because this may allow the magnetic resonance fiducial marker to be removed without removing the shaft from a subject. For instance if a physician needs to insert a large number of shafts into a subject it may not be advantageous to leave the magnetic resonance fiducial marker in place.

In another embodiment the magnetic resonance fiducial marker is adapted to be passed over a hub attached to a distal end of the shaft. This may be advantageous because the magnetic resonance fiducial marker can be removed without having to remove the shaft. The magnetic resonance fiducial markers are adapted to be removed from the shaft over the hub as distal end leaving the shaft inserted in the subject.

In another embodiment the magnetic resonance fiducial marker has a subject surface adapted for being attached to a subject with an adhesive. This is advantageous because the magnetic resonance fiducial marker may be used to identify an entry point of where the shaft enters into the subject.

In another embodiment the subject surface is sterile. For instance the magnetic resonance fiducial marker may be delivered in a sterile enclosure or package. The magnetic resonance fiducial marker may then be placed onto a sterile surface of the subject. This has the advantage of reducing the possibility of infection.

In another embodiment the magnetic resonance fiducial marker comprises a toroid. The toroid comprises a slot adapted for passing the shaft through the toroid. In some embodiments it may not be possible to pass the magnetic resonance fiducial marker over a hub. There for instance could be a slot in the toroidal structure. If there are coil structures on the toroid, then the coil structures could be adapted such that the removal of the shaft would rip apart or break a section of the coil and allow it to be removed.

In another embodiment the magnetic resonance fiducial marker comprises a toroidal magnetic resonance receive coil optionally surrounding a toroidal magnetic resonance signal volume. The advantages of this embodiment have been previously discussed.

In another embodiment the magnetic resonance fiducial marker comprises a toroidally-shaped resonant coil and capacitor. The advantages of this embodiment have also been previously discussed.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
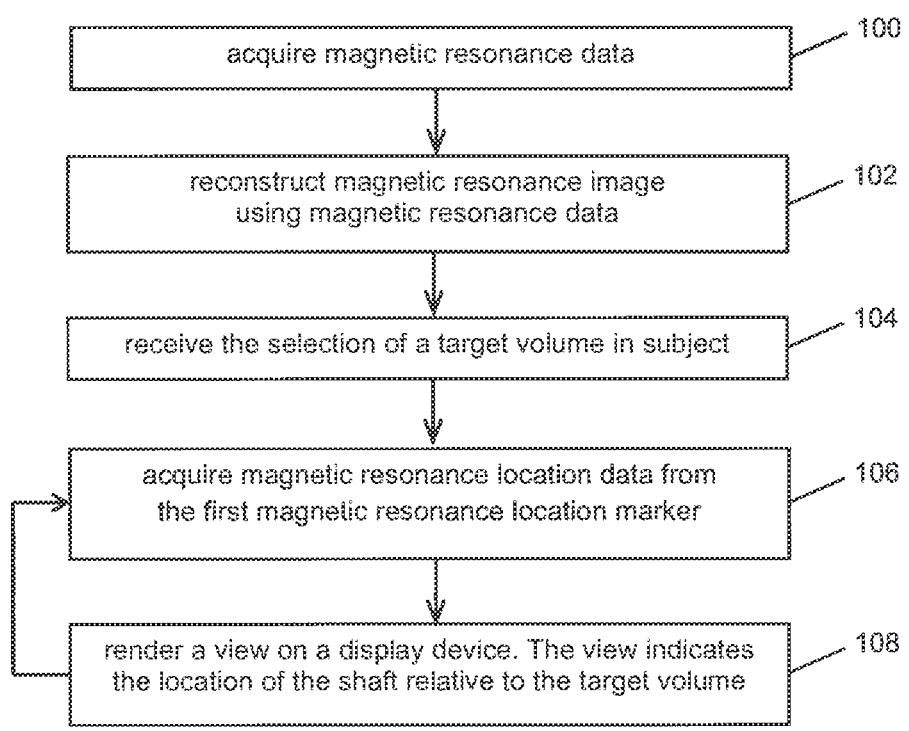
FIG. 1 shows a flow diagram which illustrates a method according to an embodiment of the invention.

FIG. 1 shows a flow diagram which illustrates a method according to an embodiment of the invention. In step 100 magnetic resonance data is acquired. In step 102 the magnetic resonance image is reconstructed using the magnetic resonance data. In step 104 the selection of a target volume in the subject is received. This for instance may be performed manually and the selection may be received from a graphical user interface. In other embodiments the target volume is identified in the magnetic resonance image automatically using a segmentation module. Next in step 106 magnetic resonance location data is acquired from the first magnetic resonance location marker. In step 108 a view is rendered on a display device. The view indicates the location of the shaft relative to the target volume. In some embodiments the magnetic resonance image is also displayed on the view. Steps 106 and 108 are repeated during a procedure using an interventional device.

Figure 2:
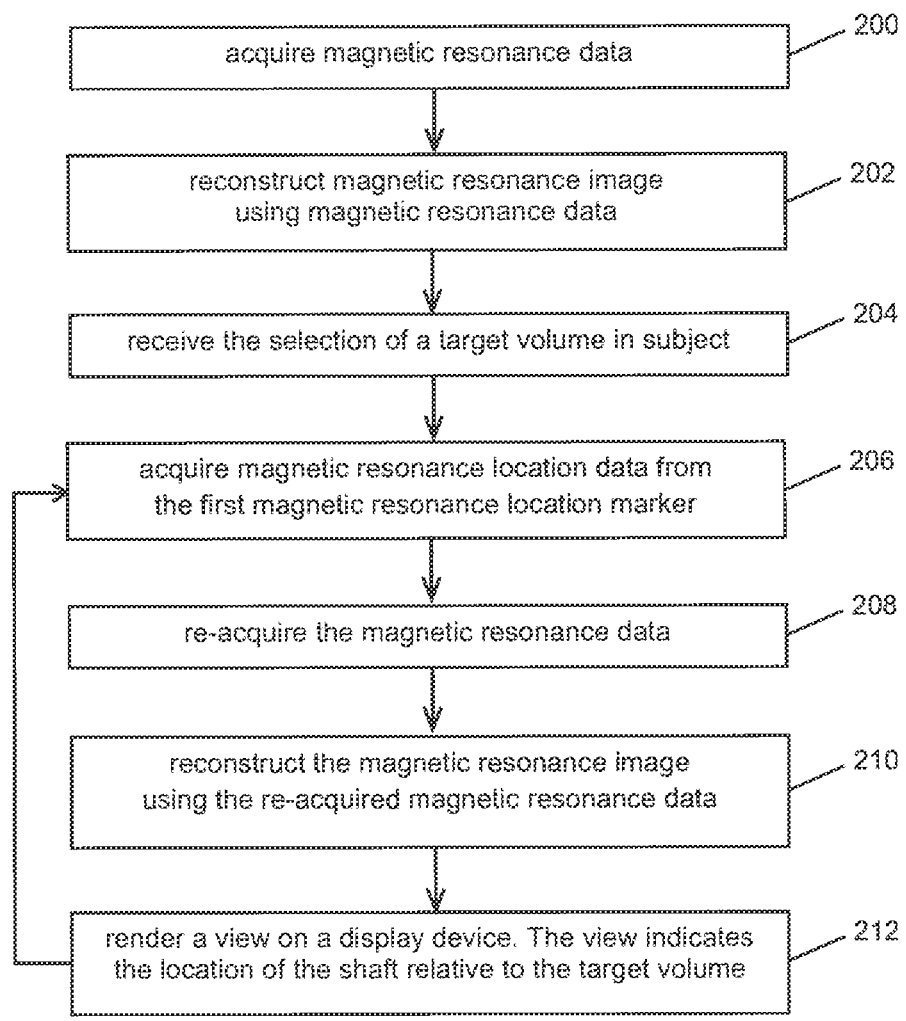
FIG. 2 shows a flow diagram which illustrates a method according to a further embodiment of the invention.

FIG. 2 shows a flow diagram which illustrates a method according to a further embodiment of the invention. In step 200 magnetic resonance data is acquired. In step 202 the magnetic resonance image is reconstructed using the magnetic resonance data. In step 204 the selection of a target volume in the magnetic resonance image is received. In step 206 magnetic resonance location data is acquired from the first magnetic resonance location marker. Next in step 208 the magnetic resonance data is re-acquired. In step 210 the magnetic resonance image is reconstructed using the re-acquired magnetic resonance data. In step 212 a view is rendered on the display device. The view indicates the location of the shaft relative to the target volume and the magnetic resonance image is displayed as a part of the view. Steps 206, 208, 210, and 212 are repeated during a procedure using the interventional device comprising a shaft.

Figures 3, 4:
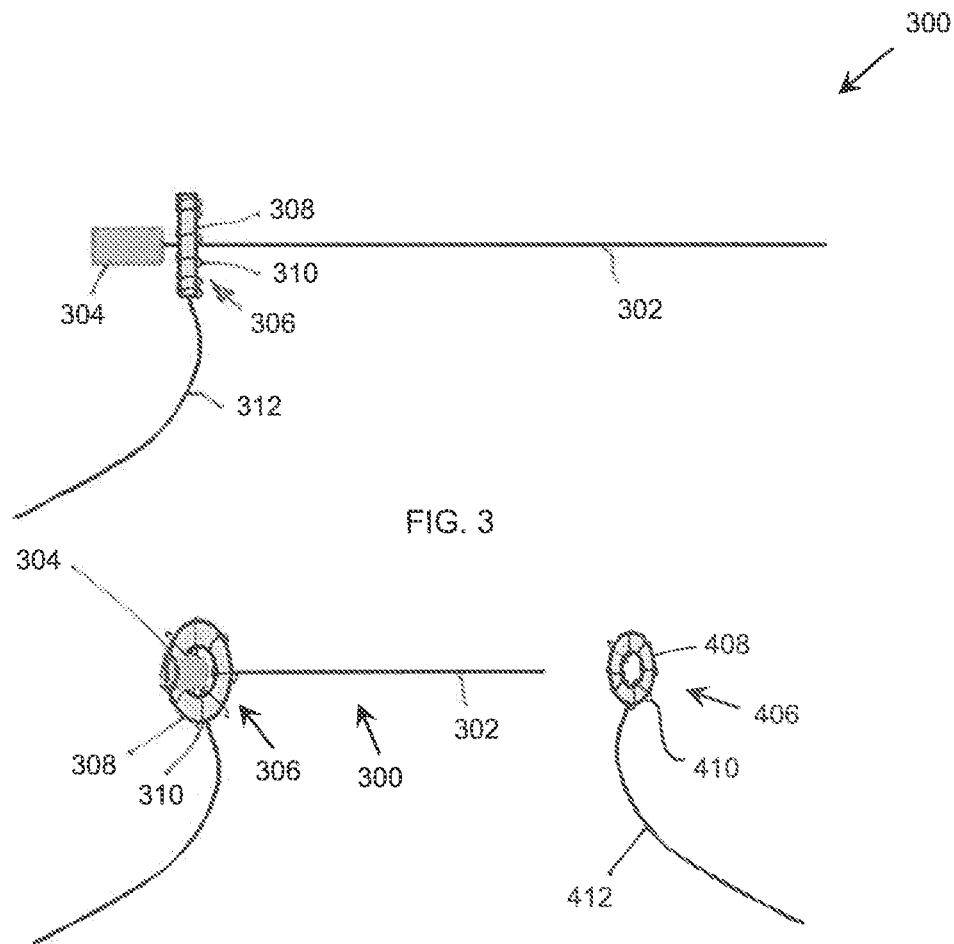
FIG. 3 illustrates an interventional device according to an embodiment of the invention.
FIG. 4 shows the interventional device of FIG. 3 in conjunction with a second magnetic resonance fiducial marker.

FIG. 3 illustrates an interventional device 300 according to an embodiment of the invention. The interventional device 300 comprises a shaft 302 or needle attached to a hub 304. Mounted on the shaft 302 is a first magnetic resonance fiducial marker 306. The first magnetic resonance fiducial marker 306 comprises a toroidal signal volume 308. There is a coil 310 wrapped around the toroidal signal volume 308. Connected to the coil 310 is a wire 312. The wire may be used for instance to connect to a pre-amplifier or other radio frequency component.

FIG. 4 shows the interventional device 300 of FIG. 3 in conjunction with a second magnetic resonance fiducial marker 406. In FIG. 3 a side view of the interventional device 300 was shown. In this Fig. the interventional device 300 is tipped at an angle. It can be seen that the hub 304 is able to pass through the centre of the toroidal first magnetic resonance fiducial marker 306. This allows for free passage or insertion of a secondary device. It also allows the first magnetic resonance fiducial marker 306 to be removed without removing the shaft 302 from a subject. The second magnetic resonance fiducial marker 406 could for instance be stuck with an adhesive to the surface of a subject. The shaft 302 would then be inserted into a centre point of the second magnetic resonance fiducial marker 406. The second magnetic resonance fiducial marker 406 has a toroidal signal volume 408. There is a coil surrounding the toroidal signal volume 408. A wire 412 is also connected to the coil 410 for the same reasons as the wire 312 is connected to the coil 310.

Figure 5:
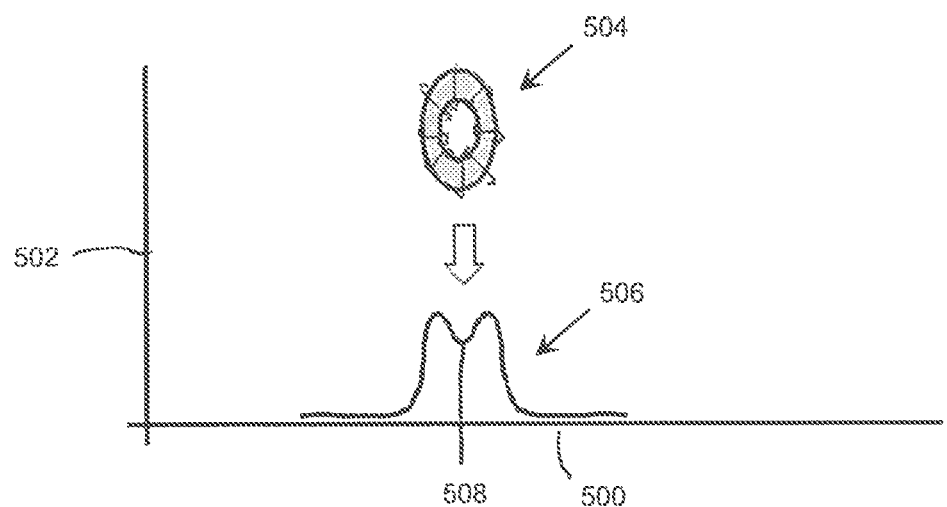
FIG. 5 illustrates a method identifying the location of the center point of a magnetic resonance fiducial marker in one spatial dimension.

FIG. 5 shows an example of how to identify the location of the magnetic resonance fiducial marker 504 using one-dimensional gradient techniques. In the plot 500 is frequency or alternatively is the spatial location. A gradient may be applied in a particular direction and a magnetic resonance signal can be measured using the magnetic resonance fiducial marker. The y-axis is labeled 502 and is the signal magnitude. 506 is a curve plotting the signal as a function of location or as a frequency. As a single gradient field is used the frequency is equivalent to the location. It can be seen that the signal has a dip at point 508. This the location of the centre point of the magnetic resonance fiducial marker 504.

Figure 6:
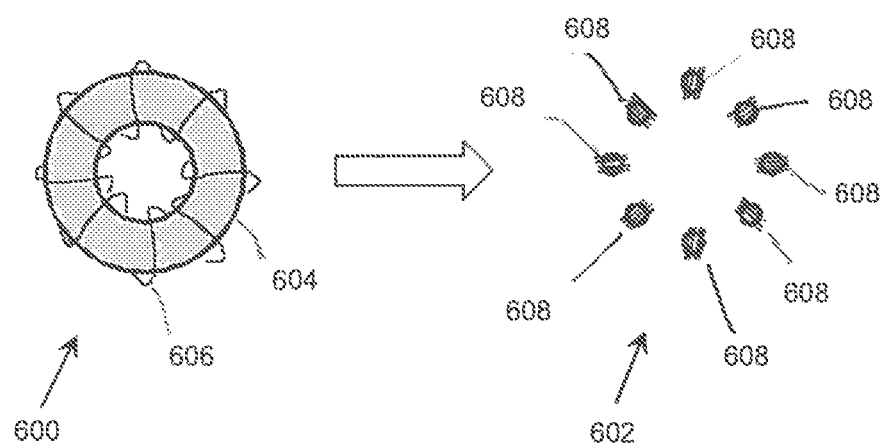
FIG. 6 illustrates two magnetic resonance fiducial markers according to embodiments of the invention.

FIG. 6 shows two examples of magnetic resonance fiducial markers 600, 602. In the example shown in FIG. 600 there is a signal volume 604 surrounded by a coil 606. In the embodiment shown in FIG. 602 there are eight solenoid coils which are wired in series 608.

Figure 7:
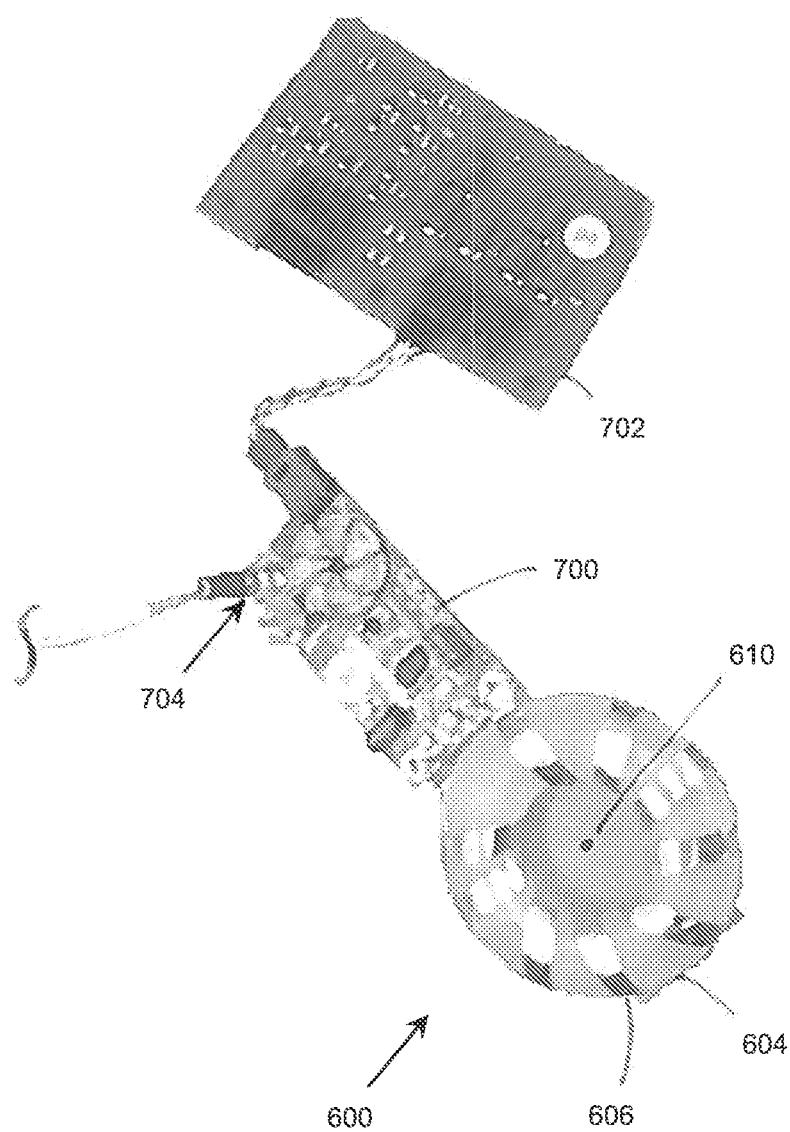
FIG. 7 illustrates a magnetic resonance fiducial marker according to a further embodiment of the invention.

FIG. 7 illustrates a magnetic resonance fiducial marker 600. Again there is a signal volume 604 surrounded by a coil 606. The magnetic resonance fiducial marker 600 has a centre point 610 for guiding a shaft. In this embodiment the magnetic resonance fiducial marker 600 is connected directly to a pre-amplifier board 700. The pre-amplifier board has a connection to a power supply board 702 and also a connection 704 for connecting to a radio frequency receiver via a radio frequency cable.

Figure 8:
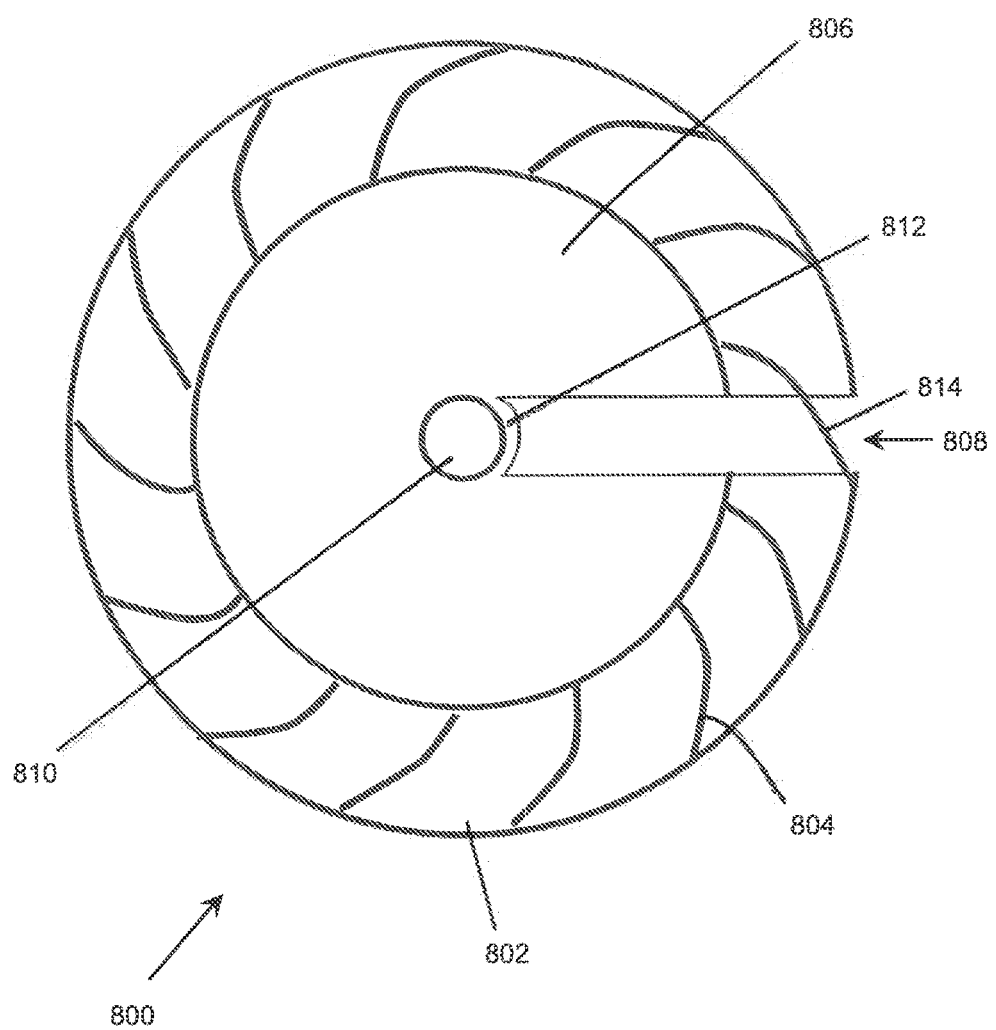
FIG. 8 shows a top view of a magnetic resonance fiducial marker according to a further embodiment of the invention.

FIG. 8 shows a top view of a magnetic resonance fiducial marker 800 according to an embodiment of the invention. The magnetic resonance fiducial marker 800 comprises a signal volume 802 surrounded by a coil 804. There is a central support 806 which has a slot or perforation 808 and a hole 810. The hole 810 is adapted for guiding a shaft. The slot 808 is through both the signal volume 802 and the central support 806. In the central support 806 there is a break area 812 which can be broken when a shaft is inserted in the hole 810. When the shaft is forced against the break area the shaft can then be moved down the slot 808. Likewise a shaft can be used to apply force to the break area of a coil 814. In this way a shaft can be removed from the magnetic resonance fiducial marker 800 without removing it from a subject.

Figure 9:
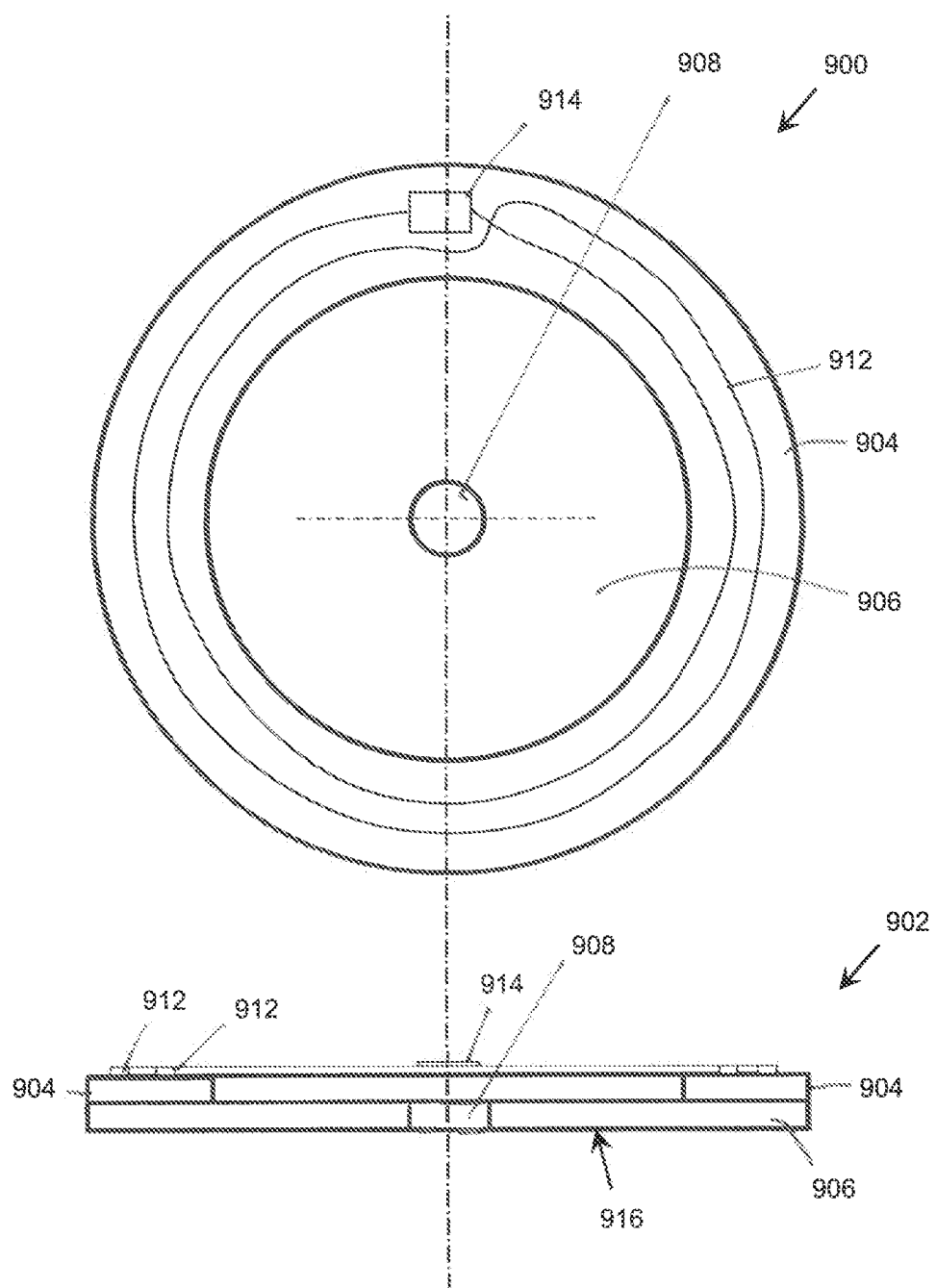
FIG. 9 shows a top and a sectional side view of a magnetic resonance fiducial marker according to a further embodiment of the invention.

FIG. 9 shows a top view 900 and a side view 902 of a further embodiment of a magnetic resonance fiducial marker according to the invention. In this embodiment there is a substrate 904 which is toroidal in shape. The substrate 904 is connected to a central support 906. There is a hole 908 in the central support 906 for guiding a shaft. On the surface of the substrate 904 there is a coil 912 in series with a capacitor 914. The coil 912 and capacitor 914 form a resonant circuit which may be detected by a magnetic resonance imaging system. The central support 906 in some embodiments may be mounted onto a subject in which case the surface 916 may be a subject surface and may also have an adhesive surface.

Figure 10:
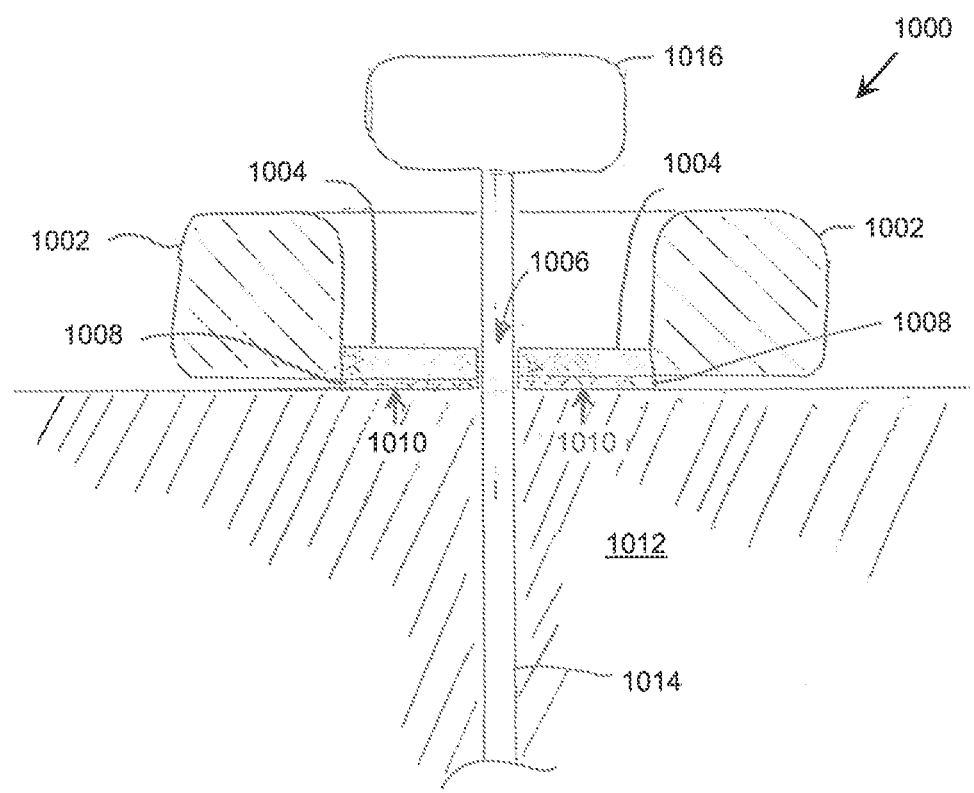
FIG. 10 shows a sectional side view of a magnetic resonance fiducial marker according to a further embodiment of the invention.

FIG. 10 shows a magnetic resonance fiducial marker 1000 according to an embodiment of the invention. In this embodiment there is a signal volume 1002. In this embodiment no coil is shown. There is a central support 1004 which is in the middle of the toroidal signal volume 1002. There is a hole 1006 in the centre of the central support 1004 for guiding a shaft 1014. There is an adhesive 1008 on the bottom of the central support 1004. In some embodiments the adhesive 1008 is also on the signal volume 1002. In yet other embodiments, the adhesive 1008 is only on signal volume 1002. The adhesive 1008 has a subject surface 1010 and is adapted for adhering to the surface of a subject 1012. A shaft 1014 is shown as being inserted through the hole 1006 and a distal end of the shaft 1014 is a hub 1016. In this embodiment the central support 1004 is able to be torn or removed from the signal volume 1002. For instance the adhesive may not be underneath the signal volume 1002 in some embodiments. When the signal volume 1002 is forcibly removed from the central support 1004 it is able to pass the hub 1016. The central part of the toroidal signal volume 1002 is larger than the circumference of the hub 1016. In this way the marker 1000 can be removed while leaving the shaft 1014 in place. Having the adhesive 1008 only on the ventral support 1004 is beneficial, because it aids in separating the signal volume from the central support 1004.

Figure 11:
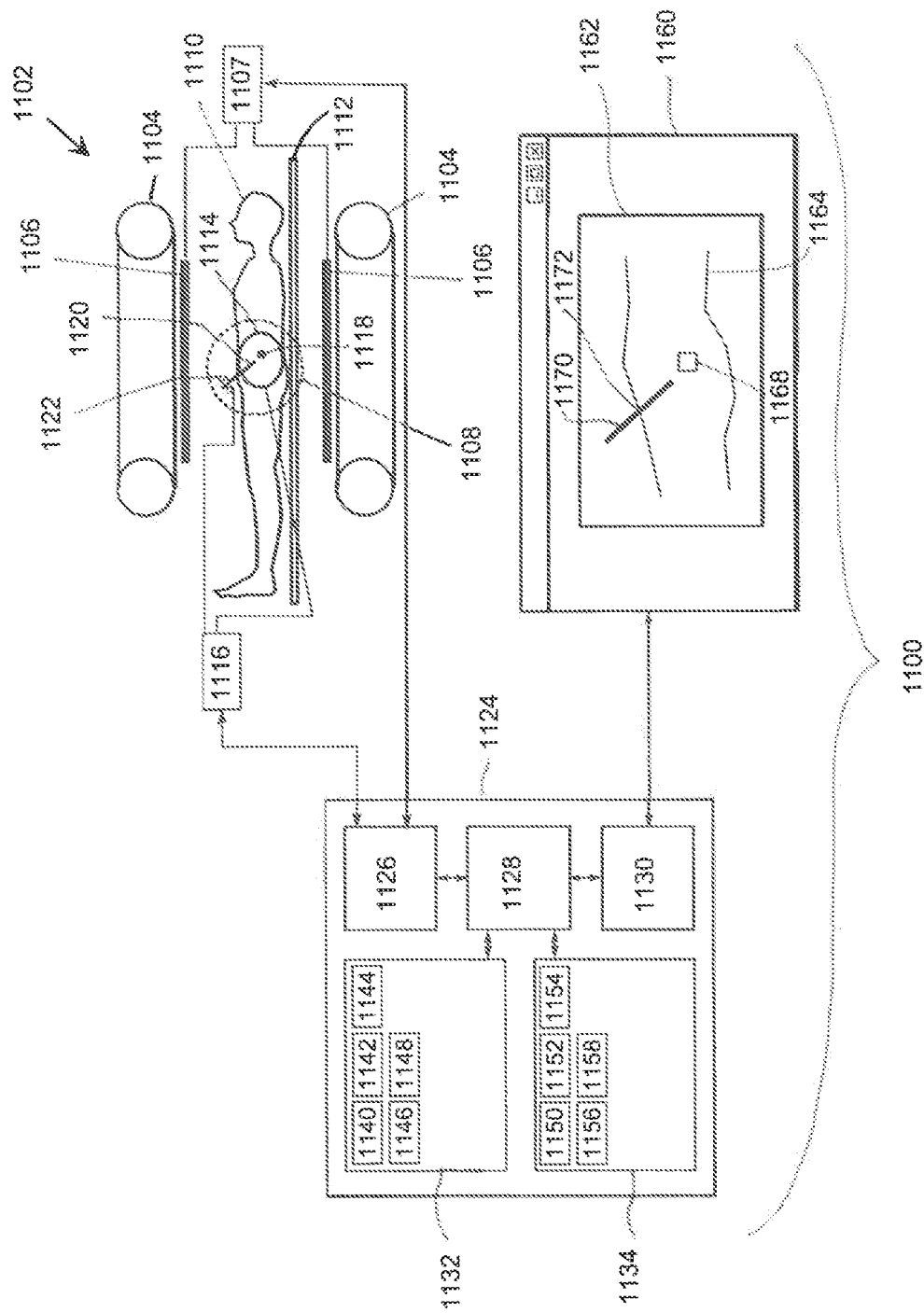
FIG. 11 illustrates a medical apparatus according to an embodiment of the invention.

FIG. 11 shows a medical apparatus 1100 according to an embodiment of the invention. The medical apparatus 1100 comprises a magnetic resonance imaging system 1102. The magnetic resonance imaging system 1102 comprises an open magnet 1104. In the open magnet two superconducting coils are mounted on top of each other and they produce a magnetic field similar to the way in which a Helmholtz coil would. The advantage to an open magnet 1104 is that it provides easy access to a subject 1110.

The magnet 1104 has a liquid helium cooled cryostat with superconducting coils. It is also possible to use permanent or resistive magnets. The use of different types of magnets is also possible for instance it is also possible to use both a split cylindrical magnet and a cylindrical magnet, although both are less convenient to use than an open magnet. A split cylindrical magnet is similar to a standard cylindrical magnet, except that the cryostat has been split into two sections to allow access to the iso-plane of the magnet. An open magnet has two magnet sections, one above the other with a space in-between that is large enough to receive a subject: as mentioned above the arrangement of the two sections is similar to that of a Helmholtz coil. Open magnets are popular, because the subject is less confined. Inside the cryostat of the cylindrical magnet there is a collection of superconducting coils. Within the magnet 1104 there is an imaging zone 1108 where the magnetic field is strong and uniform enough to perform magnetic resonance imaging.

On the inside of the magnet 1104 there are magnetic field gradient coils 1106 which are used for acquisition of magnetic resonance data to spatially encode magnetic spins within an imaging zone of the magnet. The magnetic field gradient coils 1106 are connected to a gradient coil power supply 1107. The magnetic field gradient coil is intended to be representative. Typically magnetic field gradient coils contain three separate sets of coils for spatially encoding in three orthogonal spatial directions. A magnetic field gradient power supply supplies current to the magnetic field gradient coils. The current supplied to the magnetic field coils is controlled as a function of time and may be ramped or pulsed. A subject 1110 is reposing on a subject support 1112 and is partially within the imaging zone 1108.

A surface coil 1114 can be seen as being on the surface of the subject 1110. The surface coil 1114 is a radio frequency antenna for manipulating the orientations of magnetic spins within the imaging zone and for receiving radio transmissions from spins also within the imaging zone. The surface coil 1114 is connected to a transceiver 1116. The radio frequency transceiver 1116 may be replaced by separate transmit and receive coils and a separate transmitter and receiver. It is understood that the radio frequency transceiver are simply representative. The surface coil is intended to represent a dedicated transmit antenna and a dedicated receive antenna. For instance, the magnetic resonance imaging system may also include a body coil for exciting magnetic spins. Likewise the transceiver may also represent a separate transmitter and receiver. The transceiver 1116 is a multiple channel transceiver it is connected to both a magnetic resonance marker 1122 and the surface coil 1114.

Within the subject 1110 there is a target zone 1118. A shaft or needle 1120 has been inserted into the subject 1110. There is a magnetic resonance fiducial marker 1122 on the shaft 1120. The magnetic resonance fiducial marker 1122 is also connected to the transceiver 1116. The transceiver 1116 and the gradient coil power supply 1107 are connected to a hardware interface 1126 of a computer system 1124. The computer system further comprises a processor 1128. The processor 1128 uses the hardware interface 1126 to send and receive command signals to the magnetic resonance imaging system 1102. The processor 1128 is able to control the magnetic resonance imaging system 1102 via the hardware interface 1126.

The processor 1128 is further connected to a user interface 1130, computer storage 1132, and computer memory 1134. The computer storage 1132 is shown as containing magnetic resonance data 1140. The computer storage 1132 is further shown as containing a magnetic resonance image 1142 reconstructed from the magnetic resonance data 1140. The computer storage 1132 is further shown as containing a location 1144 of the target zone 1118. These are coordinates of the target zone 1118. The computer storage 1132 is further shown as containing magnetic resonance location data 1146. The computer storage 1132 is further shown as containing an image 1148 which has been rendered and shows the relationship of the shaft 1120 relative to the target zone 1118.

The computer memory 1134 is further shown as containing a control module 1150. The control module 1150 contains computer executable code for controlling the operation and function of the medical apparatus 1100. The computer memory 1134 is further shown as containing a location identification module 1152. The location identification module 1152 is able to determine the location of magnetic resonance fiducial markers 1122 using magnetic resonance location data 1146. The computer memory 1134 is further shown as containing an image segmentation module 1154. The image segmentation module 1154 is adapted for locating target zones, shaft entry points, and/or anatomical structures using the magnetic resonance image 1142. The computer memory 1134 is further shown as containing a rendering module 1156. The rendering module 1156 is used for generating the image 1148 using at a minimum the magnetic resonance location data 1146 and the location of the target zone 1144. The computer memory 1134 is further shown as containing an image reconstruction module 1158. The image reconstruction module 1158 contains computer executable code for reconstructing the magnetic resonance image 1142 from the magnetic resonance data 1140.

As part of the user interface 1130 a graphical user interface 1160 is displayed on a display device. Within the graphical user interface 1160 is an image 1162. This may be a magnetic resonance image or it may be an image which is generated. Within the image 1162 is shown the location of a subject 1164. Within the subject 1164 is a target zone 1168. There is a needle 1170 which is also shown with its position relative to the target zone 1168. The point marked 1172 is the shaft entry point 1172 of the shaft 1120 into the subject 1110, 1164.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 300 interventional device
302 shaft
304 hub
306 first magnetic resonance fiducial marker
308 toroidal signal volume
310 coil
312 wire
406 second magnetic resonance fiducial marker
408 toroidal signal volume
410 coil
412 wire
500 frequency corresponding to spatial dimension
502 signal strength
504 magnetic resonance fiducial marker
506 signal as a function of location
508 location of center point
600 magnetic resonance fiducial marker
602 magentic resonance marker
604 signal volume
606 coil
608 solenoid coils wire in series
610 center point
700 pre-amplifier
702 power supply board
704 connection to radio-frequency receiver
800 magnetic resonance fiducial marker
802 signal volume
804 coil
806 central support
808 slot
810 hole
812 break area of central support
814 break area of coil
900 top view of magnetic resonance fiducial marker
902 side view of magnetic resonance fiducial marker
904 substrate
906 central support
908 hole
912 coil
914 capacitor
916 subject surface
1000 magnet resonance marker
1002 signal volume
1004 central support
1006 hole
1008 adhesive
1010 subject surface
1012 subject
1014 shaft
1016 hub
1100 medical apparatus
1102 magnetic resonance imaging system
1104 open magnet
1106 gradient coil
1107 gradient coil power supply
1108 imaging zone
1110 subject
1112 subject support
1114 surface coil
1116 transceiver
1118 target zone
1120 shaft
1122 magnetic resonance marker
1124 computer system
1126 hardware interface
1128 processor
1130 user interface
1132 computer storage
1134 computer memory
1140 magnetic resonance data
1142 magnetic resonance image
1144 location of target zone
1146 magnetic resonance location data
1148 image
1150 control module
1152 location identification module
1154 image segmentation module
1156 rendering module
1158 image reconstruction module
1160 graphic user interface
1162 image
1164 subject
1168 target zone
1170 shaft
1172 shaft entry point

The invention claimed is:

1. A medical system comprising:
a magnetic resonance imaging system for acquiring magnetic resonance data from a subject;
an interventional device comprising a shaft, wherein the shaft includes a distal portion that is adapted for being inserted into the subject, and a proximal portion that remains external to the subject;
a first magnetic resonance fiducial marker attached to the proximal portion of the shaft, the first magnetic resonance fiducial marker including:
a toroidal magnetic resonance signal volume that provides a first signal when the toroidal magnetic resonance signal volume is exposed to magnetic resonance signals from the magnetic resonance imaging system, and
a coil that is electromagnetically coupled to the toroidal magnetic resonance signal volume
and provides a second signal based on the first signal, wherein the shaft passes through a center point of the first magnetic fiducial marker;
a processor; and
a memory storing machine executable instructions for execution by the processor,
wherein execution of the instructions cause the processor to acquire the magnetic resonance data, wherein execution of the instructions further cause the processor to reconstruct the magnetic resonance data into a magnetic resonance image, wherein execution of the instructions further cause the processor to receive a selection of a target volume within the magnetic resonance image,
wherein execution of the instructions further cause the processor to repeatedly:
acquire magnetic resonance location data from the second signal from the coil of the first magnetic resonance fiducial marker using the magnetic resonance imaging system, wherein the magnetic resonance location data is descriptive of a location of the toroidal magnetic resonance signal volume; and render a view on a display device indicating a position of at least the distal portion of the shaft relative to the target volume when the distal portion is inserted into the subject, wherein the view is determined using at least the magnetic resonance location data and a location of the target volume.

2. The medical system of claim 1, wherein execution of the instructions further causes the processor to repeatedly:
re-acquire the magnetic resonance data;
reconstruct the magnetic resonance image using the re-acquired magnetic resonance data, wherein the view comprises the magnetic resonance image.

3. The medical system of claim 1, wherein the coil comprises a magnetic resonance receive coil surrounding the toroidal magnetic resonance signal volume.

4. The medical system of claim 1, wherein the system includes a second magnetic resonance fiducial marker that is configured to be external to the patient and is adapted for guiding the shaft through a center point of the second magnetic resonance fiducial marker, and wherein the magnetic resonance location data is further descriptive of a location of the second magnetic resonance fiducial marker.

5. The medical system of claim 4, wherein the second magnetic resonance fiducial marker comprises a magnetic resonance receive coil.

6. The medical system of claim 4, wherein the magnetic resonance location data includes the shaft position and an orientation of the shaft, and execution of the instructions further cause the processor to determine the magnetic resonance location data by:
locating a first center point of the first magnetic resonance fiducial marker and a second center point of the second magnetic resonance fiducial marker using the magnetic resonance location data; and
calculating the shaft position and orientation using at least the first and second located center points.

7. The medical system of claim 4, wherein the view is two-dimensional, wherein the second fiducial marker corresponds to a shaft entry point that is descriptive of a location where the shaft enters the subject, wherein the view is determined at least using the shaft entry point.

8. The medical system of claim 4, wherein the shaft passes through a center point of the first and second magnetic resonance fiducial marker.

9. The medical system of claim 1, wherein execution of the instructions further cause the processor to:
determine an orientation of the first magnetic resonance fiducial marker using the magnetic resonance location data; and
calculate a shaft position using at least a located center point and the orientation of the first magnetic resonance location marker.

10. The medical system of claim 1, wherein the coil includes a resonant coil and capacitor arrangement.

* * * * *